United States Patent [19]

Miyawaki

[11] Patent Number: 4,872,461
[45] Date of Patent: Oct. 10, 1989

[54] ELECTRONIC BLOOD PRESSURE METER HAVING IMPROVED CUFF REPRESSURIZATION MEANS

[75] Inventor: Yoshinori Miyawaki, Yawata, Japan

[73] Assignees: Omron Tateisi Electronics Co.; Isao KAI, both of Kyoto, Japan

[21] Appl. No.: 200,551

[22] Filed: May 31, 1988

[30] Foreign Application Priority Data

Oct. 15, 1987 [JP] Japan .................................. 62-260329

[51] Int. Cl.⁴ ............................................... A61B 5/02
[52] U.S. Cl. ..................................... 128/681; 128/682
[58] Field of Search ............................... 128/680-683; 364/413.03

[56] References Cited

U.S. PATENT DOCUMENTS

| | | | |
|---|---|---|---|
| 4,313,445 | 2/1982 | Georgi | 128/682 X |
| 4,427,013 | 1/1984 | Nunn et al. | 128/681 |
| 4,625,277 | 11/1986 | Pearce et al. | 128/683 X |
| 4,699,152 | 10/1987 | Link | 128/681 |
| 4,754,406 | 6/1988 | Miyawaki et al. | 128/681 X |
| 4,785,820 | 11/1988 | Brooks | 128/681 |

OTHER PUBLICATIONS

Knight, J. L. et al., "A Mini-Computer System for Long-Term ABP Monitoring", *Annals of Biomed Engrg.*, vol. 7, No. 3-4, 1979.

*Primary Examiner*—Francis Jaworski
*Attorney, Agent, or Firm*—Wegner & Bretschneider

[57] ABSTRACT

In an electronic blood pressure meter, pressurization requirement of the cuff is minimized by predicting a systolic blood pressure level from blood vessel information which may be obtained with an initial cuff pressure which is lower than the systolic blood pressure. The prediction of the systolic blood pressure may be based on a diastolic blood pressure, a maximum pulse wave amplitude value, on other pulse wave amplitude value, a cuff pressure value corresponding to the other pulse wave amplitude value and an empirically obtained parameter. Thus, since the cuff pressure is not increased any more than required, the discomfort to the subject person and the time period required for blood pressure measurement are both minimized and the accuracy of blood pressure measurement is improved.

16 Claims, 5 Drawing Sheets

ELECTRONIC BLOOD PRESSURE METER HAVING IMPROVED CUFF REPRESSURIZATION MEANS

TECHNICAL FIELD

The present invention relates to an improved electronic blood pressure meter which performs repressurization of the cuff when the cuff pressure is insufficient and in particular to an electronic blood pressure meter which predicts a systolic blood pressure and performs the repressurization of the cuff according to this predicted systolic blood pressure so that the cuff pressure may be raised to a sufficiently high level but no higher than required.

BACKGROUND OF THE INVENTION

An electronic blood pressure meter measures the systolic and diastolic blood pressure values of a person by wrapping a cuff around his upper arm, pressurizing or inflating this cuff to obstruct the flow of blood in his artery and obtaining blood vessel information (such as Korotkoff sound, pulse wave, eletrocardiograph, etc.). The cuff is required to be pressurized above the systolic blood pressure level and an accurate measurement is not possible if the cuff pressure is insufficient. On the other hand, excessive pressurization of the cuff not only increases the time period required for blood pressure measurement but also causes discomfort to the person whose blood pressure is to be measured.

In view of these facts, there has been proposed an electronic blood pressure meter which provisionally pressurizes the cuff to a certain pressure level and performs a repressurization when any insufficiency of the cuff pressure is detected. More specifically, when any insufficiency of the cuff pressure is detected, a certain value is added to the previous target value and the cuff is repressurized to this renewed target value.

According to this previously proposed electronic blood pressure meter, since the target value for repressurization is predetermined, the cuff pressure may continue to be insufficient even after a repressurization is performed. Therefore, depending on the circumstances, this repressurization or adjustment of an initial pressurization level may be performed a number of times before the cuff pressure reaches a sufficient level, and pressurization of the cuff for such an extended time period may cause not only discomfort to the person but also may generate measurement errors due to the hemostasis which the cuff causes in his arm. In particular, in an electronic blood pressure meter based on the detection of pulse wave as blood vessel information, since any insufficiency of cuff pressure cannot be accurately detected in an early phase of blood pressure measurement and can only be found after the cuff pressure has been reduced to the level of the diastolic blood pressure, the above mentioned problems are aggravated even further.

BRIEF SUMMARY OF THE INVENTION

In view of such problems of the prior art, a primary object of the present invention is to provide an electronic blood pressure meter which can set up an appropriate target level for repressurization of the cuff according to a prediction of a systolic blood pressure even when a first cuff pressure was found to be insufficient for measuring or computing a systolic blood pressure.

A second object of the present invention is to provide an electronic blood pressure meter which does not require more than one repressurization.

A third object of the present invention is to provide an electronic blood pressure meter which controls the cuff pressure to be no higher than required so as to minimize the cuff pressure for preventing the discomfort to the subject person and increasing the accuracy of measurement. A fourth object of the present invention is to provide an electronic blood pressure meter which permits measurement of blood pressure in a short time and can thus minimize the discomfort which the subject person experiences.

According to the present invention, these and other objects of the present invention can be accomplished by providing an electronic blood pressure meter, comprising: a cuff which can be pressurized into applying pressure to a part of a human body; pressurization means for pressurizing the cuff; a pressure sensor for detecting a pressure of the cuff; depressurization means for depressurizing the cuff; blood vessel information detecting means for detecting blood vessel information of the part of the human body; blood pressure value determining means for determining blood pressure values according to outputs from the blood vessel information detecting means and the pressure sensor; means for detecting an insufficiency of the cuff pressure according to the blood vessel information obtained by the blood vessel information detecting means; and repressurization means for activating the pressurization means when an insufficiency of the cuff pressure is detected by the cuff pressure insufficiency detecting means; further comprising: means for predicting a systolic blood pressure from the outputs from the blood vessel information detecting means and the pressure sensor; and repressurization target set-up means for defining a target value for the repressurization of the cuff according to the systolic blood pressure value predicted by the systolic blood pressure predicting means; the pressurization means being adapted to repressurize the cuff to the target value defined by the repressurization target set-up means.

It was found by the inventor of the present invention that a systolic blood pressure value can be predicted with a reasonable accuracy from the blood vessel information and the cuff pressure, and that the time period for measurement and the pain to the subject person can be minimized by repressurizing the cuff only to a level which is slightly higher than the predicted systolic blood pressure value.

According to a preferred embodiment of the present invention, the blood vessel information comprises pulse wave data obtained from the pressure sensor, and the prediction of the systolic blood pressure is based on a diastolic blood pressure value obtained by the blood pressure value determining means, a maximum pulse wave amplitude value, one other pulse wave amplitude value, a cuff pressure value corresponding to the other pulse wave amplitude value and an empirically obtained parameter.

According to a more specific aspect of the present invention, the prediction of the systolic blood pressure $P_{s^*}$ is based on the relationship given below:

$$P_{s^*} = (P_1 - P_d)/V + P_d \qquad (a)$$

$$U = (A_1/A_m) \times 100 \qquad (b)$$

$$V = V(U) \quad \text{(c)}$$

where $P_d$ is a diastolic blood pressure determined by the blood pressure determining means; $A_m$ is a maximum value of the pulse wave amplitude value; $A_1$ is the pulse wave amplitude value when the cuff pressure value is $P_1$ which is an arbitrary cuff pressure value higher than $P_d$; $V(U)$ is an empirically obtained mathematical function. The mathematical function $V(U)$ can be conveniently stored in memory of a CPU in the form of a lookup table. It was also found that a good approximation of this empirically obtained mathematical function $V(U)$ can be given by a linear approximation.

BRIEF DESCRIPTION OF THE DRAWINGS

Now the present invention is described in the following with reference to the appended drawings, in which.

DETAILED DESCRIPTION OF THE PREFERRED EMBODIMENT

The embodiment described in the following uses pulse wave data as the blood vessel information and the blood vessel information detecting means mentioned in the description of the broad concept of the present invention given above therefore corresponds to both the pulse wave detecting means and the pulse wave amplitude value computing means which are described in the following.

Figure 2:
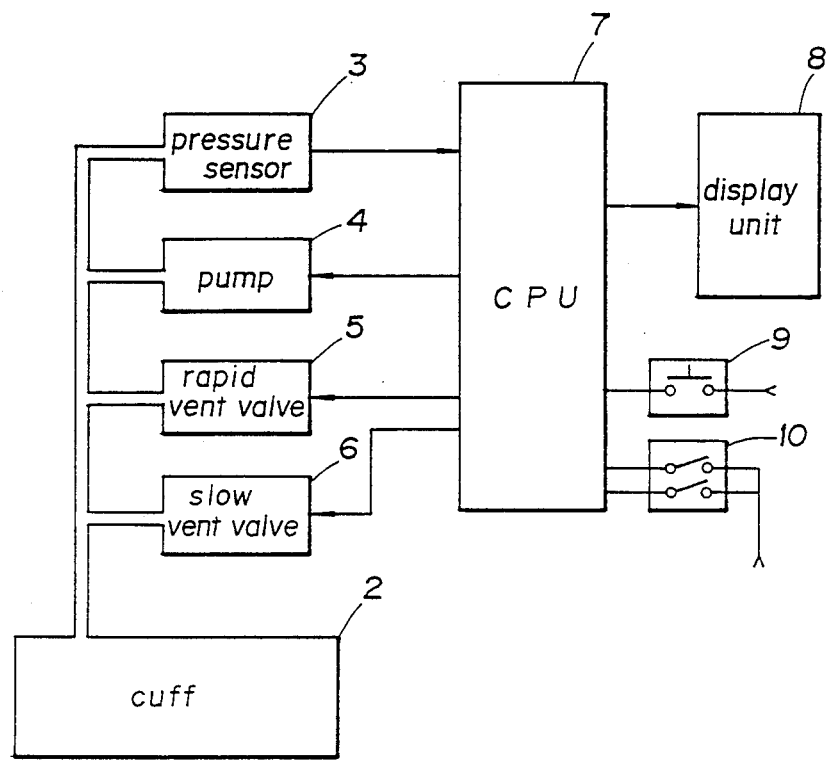
FIG. 2 is a block diagram showing the structure of the electronic blood pressure meter.

FIG. 2 is a block diagram showing the air flow system and the electronic system of an embodiment of the blood pressure meter according to the present invention. Numeral 2 denotes a cuff which is intended to be wrapped around the upper arm of a subject person as is well known in the art. To this cuff 2 are connected a pressure sensor (pressure detecting means) 3, a pump (pressurization means) 4, a rapid vent valve (depressurization means) 5, and a slow vent valve (depressurization means) 6.

The pressure sensor 3 detects the pressure inside the cuff 2 or the cuff pressure $P_c$ and its digital output is supplied to a CPU 7. The on/off control of the pump 4 as well as the control of the rapid vent valve 5 and the slow vent valve 6 is executed by the CPU 7. The CPU 7 performs the functions of detecting the pulse wave, computing the pulse wave amplitude values, determining blood pressure values, detecting the insufficiency of the cuff pressure, computing parameters and determining a target value for repressurization. The CPU 9 is connected to an LCD display unit 8 for displaying the blood pressure values determined by the CPU 7.

The CPU 7 is further connected to a start switch 9 and a pressurization target value set-up switch 10. The start switch 9 is for starting blood pressure measurement while the pressurization target value set-up switch 10 is for setting up a initial target value for pressurization. This pressurization target value set-up switch 10 can be omitted if desired.

Now the action of this blood pressure meter of the present embodiment is described in the following.

Figure 1A:
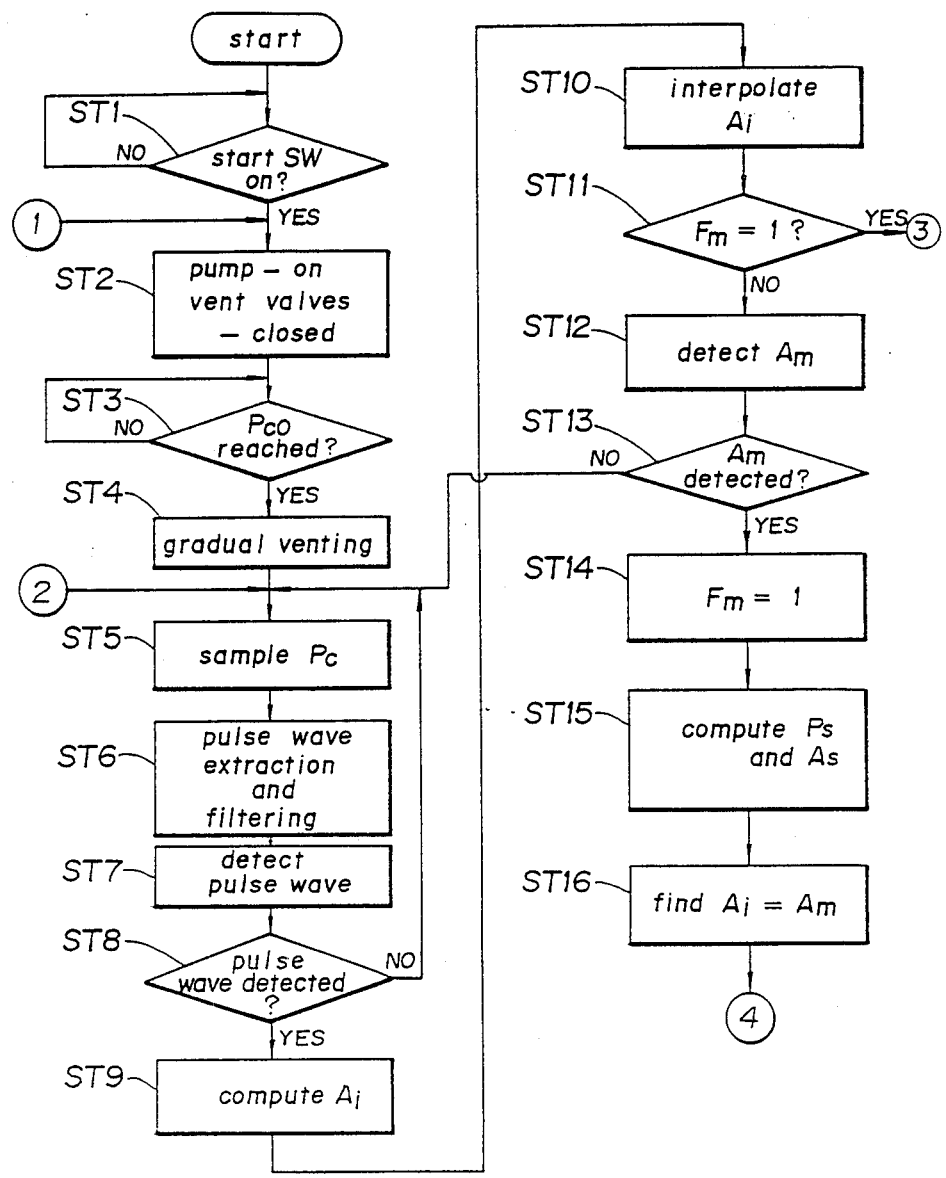
FIGS. 1(a) and 1(b) are flow charts showing the action of an embodiment of the electronic blood pressure meter according to the present invention.

As shown in FIG. 1(a), when the power is turned on, it is determined whether the start switch 9 has been turned on or not (ST 1). The determination process of ST 1 is continued until the start switch 9 is finally turned on. The start switch 9 is turned on after the cuff 2 is wrapped around the upper arm of the subject person and an initial target value for pressurization $P_{c0}$ is set by the switch 10. This is detected in the determination step of ST 1 and the system flow advances to ST 2 where the CPU 7 activates the pump 4 and closes both the rapid vent valve 5 and the slow vent valve 6 to start the pressurization of the cuff 2.

In ST 3, it is determined whether the cuff pressure $P_c$ has reached the initial target value $P_{c0}$ or not. This step is repeated until the cuff pressure reaches this target value. When the target value has been reached, the system flow advances to ST 4 where the pump 4 is deactivated and the slow vent valve 6 is opened so as to start the gradual depressurization of the cuff 2.

Figure 3:
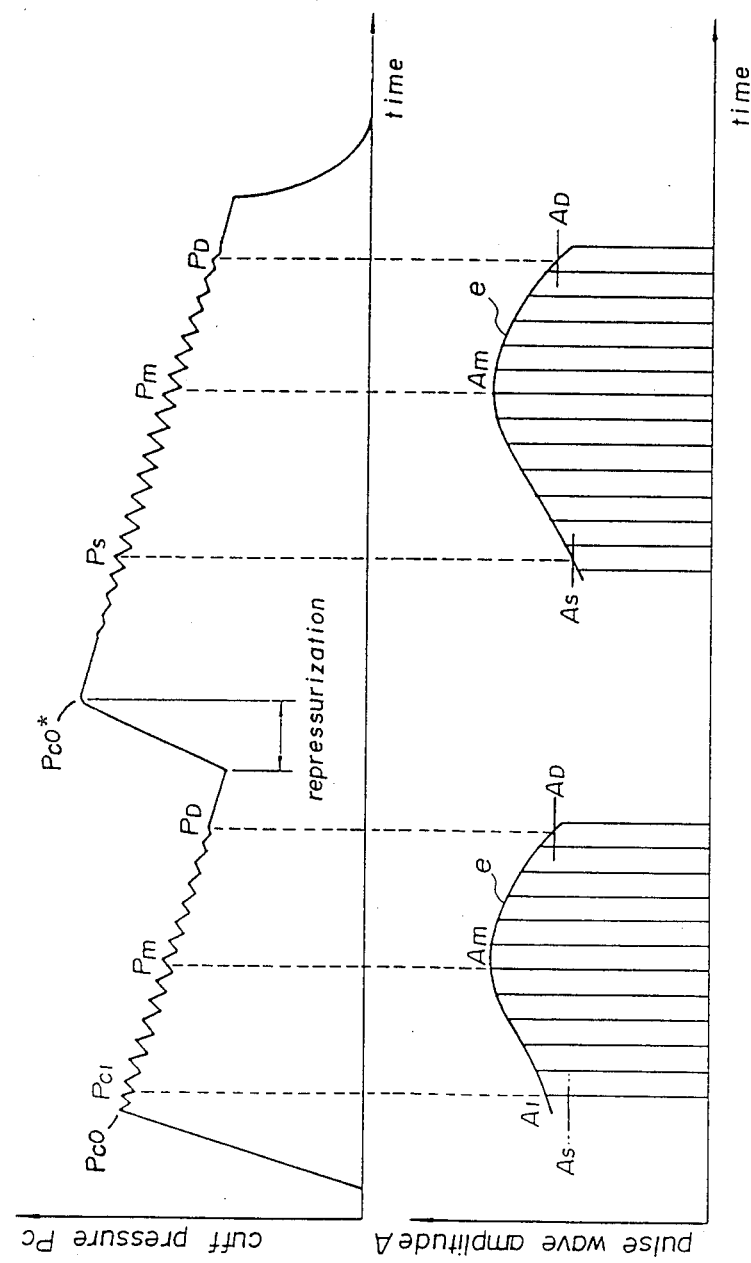
FIG. 3 is a graph showing typical changes in the cuff pressure and the pulse wave amplitude with time.

In ST 5, the cuff pressure $P_c$ is measured at a certain sampling interval (normally from 10 msec to 50 msec). In ST 6, this cuff pressure data is passed through a high-pass or band-pass digital filter and the AC component or the pulse wave component contained in the cuff pressure data is extracted (See FIG. 3 also). This pulse wave component is an oscillatory signal with respect to a certain reference level, and detection of a pulse wave is defined as detection of a pulse wave signal which exceeds a certain threshold level (ST 7). This threshold level may be in the order of 0.3 to 1.0 mmHg when blood pressure measurement is made on the upper arm of a subject person.

In ST 8, it is determined whether a pulse wave was detected in ST 7 or not. If a pulse wave was not detected, the system flow then returns to ST 5 and the detection of a pulse wave is repeated. If a pulse wave is detected in ST 7, the system flow proceeds from ST 8 to ST 9 and the amplitude $A_i$ of the pulse wave is computed. This pulse wave amplitude $A_i$ is computed for every pulse or from a point of intersection of a rising pulse wave signal level with the threshold level to the next point, as a difference between the maximum and the minimum of the pulse wave signal level within this interval (See FIG. 3 also).

An interpolation is performed between each current pulse wave amplitude value $A_i$ and the preceding pulse wave wave amplitude value $A_{i-1}$ (ST 10). In other words, an envelope $e0$ is obtained by smoothly connecting the peaks of the pulse wave amplitude level.

In ST 11, it is determined whether a maximum pulse wave amplitude value detection flag $F_m$ is 1 or 0. The flag $F_m$ remains to be 0 until a maximum pulse wave amplitude value $A_m$ is detected as described hereinafter. When this maximum pulse wave amplitude value $A_m$ has already been detected, the system flow advances from ST 11 to ST 12. Otherwise, the system flow advances from ST 11 to ST 21 which is described hereinafter.

In ST 12, a maximum pulse wave amplitude value $A_m$ is selected from all the pulse wave amplitude values which have been obtained so far. The pulse wave amplitude value keeps increasing until the average blood pressure $P_m$ is obtained and, thereafter, gradually decreases (See FIG. 3). Therefore, when a decrease of the pulse wave amplitude value is detected, it means that the maximum pulse wave amplitude value $A_m$ has already been obtained and all that is required here is to select the largest value of all the pulse wave amplitude values which have so far been obtained. In ST 13, it is determined whether the maximum pulse wave amplitude value $A_m$ was obtained in ST 12 or not, and if not, the system flow returns to ST 5 and the detection of pulse wave is continued. If the determination result of ST 13 is affirmative, the system flow advances to ST 14 where the maximum pulse wave amplitude value detection flag $F_m$ is set to 1.

In ST 15, a pulse wave amplitude value $A_s$ for determining a systolic blood pressure is computed. This pulse wave amplitude value $A_s$ may be computed, for instance as given by Equation (3) given below:

$$A_s = (A_m - 0.5 \text{ mmHg})/0.6 \quad (3)$$

Then, an amplitude which is equal to the amplitude value $A_s$ is detected from the pulse wave data which corresponds to a cuff pressure higher than the average blood pressure $P_m$ (or which precedes the appearance of the maximum pulse wave amplitude value $A_m$) (ST 16).

Figure 1B:
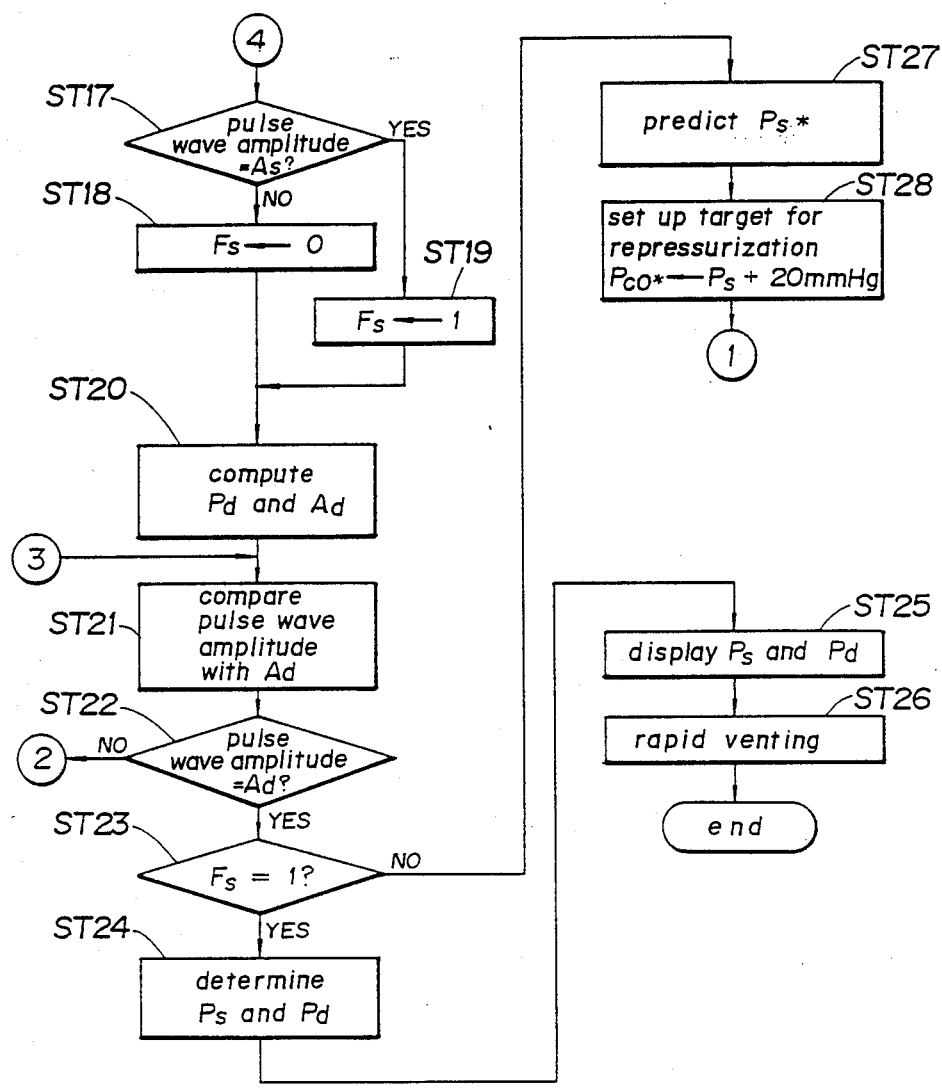

In ST 17, it is determined whether a pulse wave amplitude equal to the amplitude value $A_s$ has been detected or not (See FIG. 1(b)). $A_s$ shown in the left half of FIG. 3, such an amplitude (which is equal to the amplitude value $A_s$) may not be detected if the initial cuff pressure was insufficient. If that was the case, the determination result of ST 17 therefore becomes negative and an $A_s$ detection flag $F_s$ is set to zero (ST 18). On the other hand, if the determination result of ST 17 is affirmative, the $A_s$ detection flag $F_s$ is set to one. Thus, the $A_s$ detection flag serves as an index for indicating whether the initial cuff pressure $P_{c0}$ was sufficient or not.

The system flow advances from ST 18 or ST 19 to ST 20 where the pulse wave amplitude value $A_d$ for determining a diastolic blood pressure $P_d$ is computed. This pulse wave amplitude value $A_d$ may be computed, for instance as given by Equation (4) given below:

$$A_d = (A_m - 0.5 \text{ mmHg})/0.7 \quad (4)$$

Then, an amplitude which is equal to the amplitude value $A_d$ is detected from the pulse wave data which corresponds to a cuff pressure lower than the average blood pressure $P_m$ (or which follows the appearance of the maximum pulse wave amplitude value $A_m$) (ST 21). In ST 22, it is determined whether an amplitude equal to the amplitude value $A_d$ has been detected or not. If the result of this determination step is negative, the system flow returns for ST 5 and the detection of the pulse wave is continued. Since the steps of ST 12 through ST 20 are not required in the subsequent processes of detecting the pulse wave and computing pulse wave amplitude values, the system flow directly advances from ST 11 to ST 21 (the determination result of ST 11 becomes negative since the flag $F_m$ was set to 1 in ST 14).

When the determination result of ST 22 is affirmative, the system flow advances to ST 23 and it is determined whether the flag $F_s$ is 1 or zero. If this flag $F_s$ is 1 or, in other words, if the cuff pressure is found to be sufficient, the system flow advances to ST 24 where a systolic blood pressure $P_s$ and a diastolic blood pressure $P_d$ are determined. The systolic blood pressure $P_s$ is determined as the cuff pressure which corresponds to the pulse wave amplitude $A_s$ while the diastolic blood pressure $P_d$ is determined as the cuff pressure which corresponds to the pulse wave amplitude $A_d$.

In subsequent ST 25, the systolic blood pressure $P_s$ and the diastolic blood pressure $P_d$ are displayed on the display unit 8. At the same time, the rapid vent valve 26 is opened and the cuff 2 is rapidly depressurized to complete the blood pressure measurement.

On the other hand, if the determination result of ST 23 is negative or, in other words, if the cuff pressure is found to be insufficient, the system flow advances to ST 27 and the process of predicting the systolic blood pressure $P_s$ is executed.

This prediction process is based on the first pulse wave amplitude value $A_1$, the cuff pressure $P_c$ corresponding to this first pulse wave amplitude value $A_1$, the maximum pulse wave amplitude value $A_m$ and the diastolic blood pressure $P_d$. Parameters U and V given by following equations (1) and (2) are related to each other as given by a curve C shown in FIG. 4.

$$U = (A_1/A_m) \times 100 \quad (1)$$

$$V = (P_1 - P_d)/(P_s - P_d) \quad (2)$$

Figure 4:
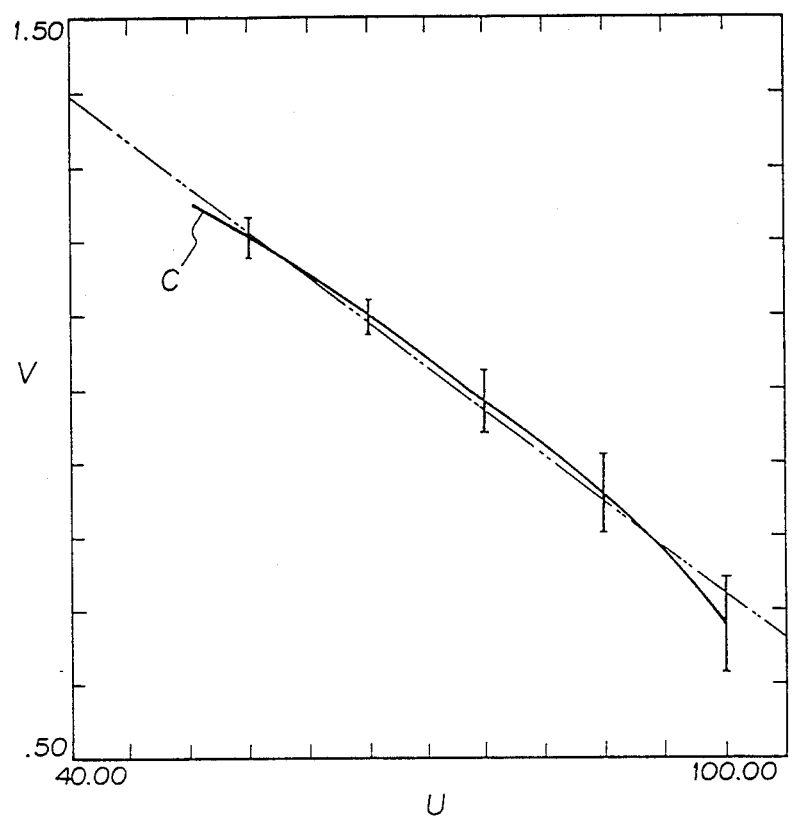
FIG. 4 is a graph showing a relationship between certain parameters.

The graph of FIG. 4 was empirically obtained from statistical data of a large number of people. The vertical lines shown along the curve indicate the spreads of standard deviation.

The relationship given by the curve C is stored in the memory of the CPU 7 as a lookup table, and a value of V can be looked up when a value of U is given. Once a value of V is obtained, a predicted value of systolic blood pressure $P_{s*}$ can be computed from Equation (2') given below:

$$P_{s*} = (P_1 - P_d)/V + P_d \quad (2')$$

Now an example of error involved in this prediction process is given in the following. The standard deviation of the value V becomes greatest when $U = 95$. In this case, the standard deviation is 0.07 and it amounts to 12 mmHg in the worst case if $P_1 = 120$ mmHg, $P_d = 60$ mmHg and an error of twice the standard deviation of V is assumed.

Instead of storing the curve C in the form of a full lookup table in the memory of the CPU 7, it is possible to use a linear approximation given by chain-double-dot line shown in FIG. 4. This line was obtained as a result of a regression analysis of actual data and may be given by Equation (5) given below.

$$V = -0.189U + 1.89 \quad (5)$$

In subsequent ST 28, a target value of repressurization $P_{c0*}$ is computed from the systolic blood pressure value $P_{s*}$ predicted in ST 27 according to the following formula.

$$P_{c0*} = P_{s*} + 20 \text{ mmHg} \quad (6)$$

However, it is also possible to compute a target value of repressurization $P_{c0*}$ in different manners.

When the process of ST 28 is completed, the system flow returns to ST 2 to repressurize the cuff and determine a systolic blood pressure $P_s$ and a diastolic blood pressure $P_d$. When this repressurization is performed, as shown in the right half of FIG. 3, the cuff pressure is increased over a systolic blood pressure level and complete pulse wave data can be now obtained. In other words, the pulse wave data contains the data corresponding to the pulse wave amplitude $A_s$ and a systolic blood pressure can be obtained without requiring any further repressurization.

Thus, since the cuff pressure is not increased any more than required, the discomfort to the subject person and the time period required for blood pressure measurement are both minimized and the accuracy of blood pressure measurement is improved.

In the above described embodiment, the blood vessel information consisted of pulse wave data, but the present invention can also be applied to electronic blood pressure meters of other types which may be based on the detection of the Korotkoff sound and electrocardiograph.

Although the present invention has been shown and described with reference to the preferred embodiment thereof, it should not be considered as limited thereby. Various possible modifications and alterations could be conceived of by one skilled in the art to any particular detail of the embodiment, without departing from the scope of the invention.

What we claim is:

1. An electronic blood pressure meter, comprising:
   a cuff which can be pressurized into applying pressure to a part of a human patient;
   pressurization means for pressurizing the cuff, wherein said pressurization means initially pressurizes the cuff to an initial cuff pressure which may or may not be above the systolic pressure of said patient;
   depressurization means for depressurizing the cuff;
   pressure sensing means for detecting a pressure of the cuff while said depressurization means is depressurizing said cuff and for providing an output thereof;
   blood vessel information detecting means for detecting blood vessel information of the part of the human patient and for providing an output thereof;
   detecting means for detecting, based on said blood vessel information, whether the initial cuff pressure was below the systolic pressure of the patient;
   predicting mean, responsive to detection of a sub-systolic initial cuff pressure, for computing a predicted systolic pressure value from the outputs of the pressure sensing means and from the blood vessel information detecting means;
   repressurization level determining means for determining a repressurization level based on the predicted systolic pressure value computed by said predicting means if said detecting means detects a sub-systolic initial cuff pressure;
   repressurization means for instructing said pressurization means to pressurize said cuff to said repressurization level if said detecting means detects a sub-systolic initial cuff pressure; and
   blood pressure value determining means for determining systolic and diastolic pressure values according to said outputs from the blood vessel information detecting means and the pressure sensing means.

2. The electronic blood pressure meter as claimed in claim 1, wherein the blood vessel information comprises pulse wave data obtained from the pressure sensor, further comprising means for determining a maximum pulse wave amplitude, means for determining one other pulse wave amplitude, means for determining a cuff pressure value corresponding to said one other pulse wave amplitude, and means for obtaining an empirically determined parameter, and wherein said predicted systolic pressure is predicted using said diastolic pressure value, said maximum pulse wave amplitude, said one other pulse wave amplitude, said cuff pressure value which corresponds to said one other pulse wave amplitude, and said empirically determined parameter.

3. The electronic blood pressure meter as claimed in claim 2, wherein said predicted systolic pressure value is determined according to the following relationships:

$$P_{s*} = (P_1 - P_d)/V + P_d;$$

$$U = (A_1/A_m) \times 100; \text{ and}$$

$$V = V(U);$$

wherein
   $P_{s*}$ is the predicted systolic pressure value;
   $P_d$ is the diastolic pressure value;
   $A_m$ is the maximum pulse wave amplitude;
   $A_1$ is the one other pulse wave amplitude;
   $P_1$ is the cuff pressure value which corresponds to the one other pulse wave amplitude; and
   V(U) is an empirically determined mathematical function from which is empirically determined parameter is obtained.

4. The electronic blood pressure meter as claimed in claim 3, comprising a CPU having a memory which defines a lookup table, wherein said mathematical function V(U) is stored in said lookup table.

5. The electronic blood pressure meter as claimed in claim 3, wherein said mathematical function V(U) is given by a linear approximation.

6. A method for measuring blood pressure, comprising:
   attaching a cuff which can be pressurized to a part of a human patient;
   pressurizing the cuff, wherein said cuff is initially pressurized to an initial cuff pressure which may or may not be above the systolic pressure of said patient;
   depressurizing the cuff;
   detecting a pressure of the cuff while said cuff is depressurized and providing an output corresponding thereto;
   detecting blood vessel information of the part of the human patient and providing an output corresponding thereto;
   detecting, based on said blood vessel information, whether the initial cuff pressure was below the systolic pressure of the patient;
   computing, upon detection of a sub-systolic initial cuff pressure, a predicted systolic pressure value from the outputs of the pressure sensing step and from the blood vessel information detecting step;
   determining a repressurization level based on the predicted systolic pressure value computed in said predicting step if a sub-systolic initial cuff pressure is detected;
   pressurizing said cuff to said repressurization level if a sub-systolic initial cuff pressure is detected; and
   determining systolic and diastolic pressure values according to said outputs from the blood vessel information detecting step and the pressure sensing step.

7. The method as claimed in claim 6, wherein the blood vessel information comprises pulse wave data obtained from the pressure sensor, further comprising determining a maximum pulse wave amplitude, determining one other pulse wave amplitude, determining a cuff pressure value corresponding to said one other pulse wave amplitude, and obtaining an empirically determined parameter, and wherein said predicted systolic pressure is predicted using said diastolic pressure value, said maximum pulse wave amplitude, said one other pulse wave amplitude, said cuff pressure value which corresponds to said one other pulse wave amplitude, and said empirically determined parameter.

8. The method as claimed in claim 7, wherein said predicted systolic pressure value is determined according to the following relationships:

$$P_{s*} = (P_1 - P_d)/V + P_d;$$

$$U = (A_1/A_m) \times 100; \text{ and}$$

$$V = V(U);$$

wherein
$P_{s*}$ is the predicted systolic pressure value;
$P_d$ is the diastolic pressure value;
$A_m$ is the maximum pulse wave amplitude;
$A_1$ is the one other pulse wave amplitude;
$P_1$ is the cuff pressure value which corresponds to the one other pulse wave amplitude; and
$V(U)$ is an empirically determined mathematical function from which said empirically determined parameter is obtained.

9. The method as claimed in claim 8, wherein said mathematical function $V(U)$ is stored in a lookup table defined in a memory of a CPU.

10. The method as claimed in claim 8, wherein said mathematical function $V(U)$ is given by a linear approximation.

11. An electronic blood pressure meter, comprising:
a cuff which can be pressurized into applying pressure to a part of a human patient;
pressurization means for pressurizing the cuff, wherein said pressurization means initially pressurizes the cuff to an initial cuff pressure;
depressurization means for depressurizing the cuff;
pressure sensing means for detecting a pressure of the cuff while said depressurization means is depressurizing said cuff and for providing an output thereof;
pulse wave data detecting means for detecting pulse wave data of the part of the human patient and for providing an output thereof;
means for determining a diastolic pressure value according to said outputs from the pulse wave data detecting means and the pressure sensing means;
means for determining a maximum pulse wave amplitude;
means for determining one another pulse wave amplitude;
means for determining a cuff pressure value corresponding to said one other pulse wave amplitude;
means for obtaining an empirically determined parameter; and
predicting means for computing a predicted systolic pressure value according to the following relationships:

$$P_{s*} = (P_1 - P_d)/V + P_d;$$

$$U = (A_1/A_m) \times 100; \text{ and}$$

$$V = V(U);$$

wherein
$P_{s*}$ is the predicted systolic pressure value;
$P_d$ is the diastolic pressure value;
$A_m$ is the maximum pulse wave amplitude;
$A_1$ is the one other pulse wave amplitude;
$P_1$ is the cuff pressure value which corresponds to the one other pulse wave amplitude; and
$V(U)$ is an empirically determined mathematical function from which said empirically determined parameter is obtained.

12. The electronic blood pressure meter as claimed in claim 11, comprising a CPU having a memory which defines a lookup table, wherein said mathematical function $V(U)$ is stored in said lookup table.

13. The electronic blood pressure meter as claimed in claim 11, wherein said mathematical function $V(U)$ is given by a linear approximation.

14. A method for measuring blood pressure, comprising:
applying a cuff which can be pressurized to a part of a human patient;
pressurizing the cuff, wherein said cuff is initially pressurizing to an initial cuff pressure;
depressurizing the cuff;
detecting a pressure of the cuff while said cuff is depressurized and providing an output corresponding thereto;
detecting pulse wave data of the part of the human patient and providing an output corresponding thereto;
determining a diastolic pressure value according to said outputs from the pulse wave data detecting step and the pressure sensing step;
determining a maximum pulse wave amplitude;
determining one other pulse wave amplitude;
determining a cuff pressure value corresponding to said one other pulse wave amplitude;
obtaining an empirically determined parameter; and
computing a predicted systolic pressure value according to the following relationships:

$$P_{s*} = (P_1 - P_d)/V + P_d;$$

$$U = (A_1/A_m) \times 100; \text{ and}$$

$$V = V(U);$$

wherein
$P_{s*}$ is the predicted systolic pressure value;
$P_d$ is the diastolic pressure value;
$A_m$ is the maximum pulse wave amplitude;
$A_1$ is the one other pulse wave amplitude;
$P_1$ is the cuff pressure value which corresponds to the one other pulse wave amplitude; and
$V(U)$ is an empirically determined mathematical function from which said empirically determined parameter is obtained.

15. The method as claimed in claim 14, wherein said mathematical function $V(U)$ is stored in a lookup table defined by a memory by a CPU.

16. The method as claimed in claim 14, wherein said mathematical function $V(U)$ is given by a linear approximation.

* * * * *